US00PP22513P2

(12) United States Plant Patent
Clifford et al.

(10) Patent No.: US PP22,513 P2
(45) Date of Patent: Feb. 21, 2012

(54) ***DIANTHUS* PLANT NAMED 'FAITH'**

(50) Latin Name: *Dianthus gratianopolitanus*
Varietal Denomination: Faith

(76) Inventors: John K. Clifford, Paw Paw, MI (US); Ken J. Clifford, Paw Paw, MI (US)

( * ) Notice: Subject to any disclaimer, the term of this patent is extended or adjusted under 35 U.S.C. 154(b) by 0 days.

(21) Appl. No.: 12/932,092

(22) Filed: Feb. 17, 2011

(51) Int. Cl.
*A01H 5/00* (2006.01)

(52) U.S. Cl. ..... Plt./272

(58) Field of Classification Search ..... Plt./272, Plt./276, 281
See application file for complete search history.

*Primary Examiner* — Kent L Bell
(74) *Attorney, Agent, or Firm* — Penny J. Aguirre

(57) ABSTRACT

A new cultivar of *Dianthus gratianopolitanus,* 'Faith', characterized by its variegated foliage with blue-green centers and creamy white margins with the center color becoming more blue as the season progresses, its flowers that are light pink in color with a small white eye, its compact plant habit, and blooming period in mid spring.

2 Drawing Sheets

Botanical classification: *Dianthus gratianopolitanus.*
Variety denomination: 'Faith'.

BACKGROUND OF THE INVENTION

The present invention relates to a new and distinct cultivar of *Dianthus* plant, botanically known as *Dianthus gratianopolitanus* 'Faith' and will be referred to hereinafter by its cultivar name, 'Faith'. The new cultivar represents a new cultivar of cheddar pink, an herbaceous perennial grown for landscape use.

'Faith' was discovered in a container block by the inventors in a nursery in Lewisburg, Tenn. in April of 2007. The new cultivar arose as a naturally occurring chimeral mutation that arose during propagation of *Dianthus gratianopolitanus* 'Firewitch' (not patented).

Asexual reproduction of the new cultivar was first accomplished using basal stem cuttings in June of 2007 in Paw Paw, Mich. Propagation by stem cuttings and in vitro propagation has determined that the characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Faith' as unique from all other varieties of *Dianthus* known to the inventors.

1. 'Faith' exhibits foliage that is variegated with blue-green centers and creamy white margins with the center color becoming more blue as the season progresses.
2. 'Faith' exhibits flowers that are light pink in color with a small white eye.
3. 'Faith' exhibits a compact plant habit.
4. 'Faith' blooms for about 3 weeks in mid spring.

'Faith' differs from its parent plant, 'Firewitch' in having variegated foliage, in having flowers that are more pink and less bright in color, in blooming slightly later in the season, and in being more compact. 'Faith' can be most closely compared to other cultivars that are also chimeral mutations of 'Firewitch', 'Bewitched' (U.S. Plant Pat. No. 13,159) and 'Wicked Witch' (U.S. Plant Pat. No. 19,824). 'Bewitched' differs from 'Faith' in lacking variegated foliage and in having pink flowers with a small burgundy eye. 'Wicked Witch' differs from 'Faith' in lacking variegated foliage and in having flowers that are cherry red in color. 'Faith' can also be compared to 'Bath's Pink' (not patented), which is similar to 'Faith' in having light pink flowers and in bloom period. 'Faith Pink' differs from 'Bath's' in having a much less compact plant habit and in lacking variegated foliage.

BRIEF DESCRIPTION OF THE DRAWING

The accompanying colored photographs illustrate the overall appearance and distinct characteristics of the new *Dianthus.* The photographs in the figures were taken of a plant about 12 months in age as grown outside in a 1-quart container in Lewisburg, Tenn.

Figure 1:
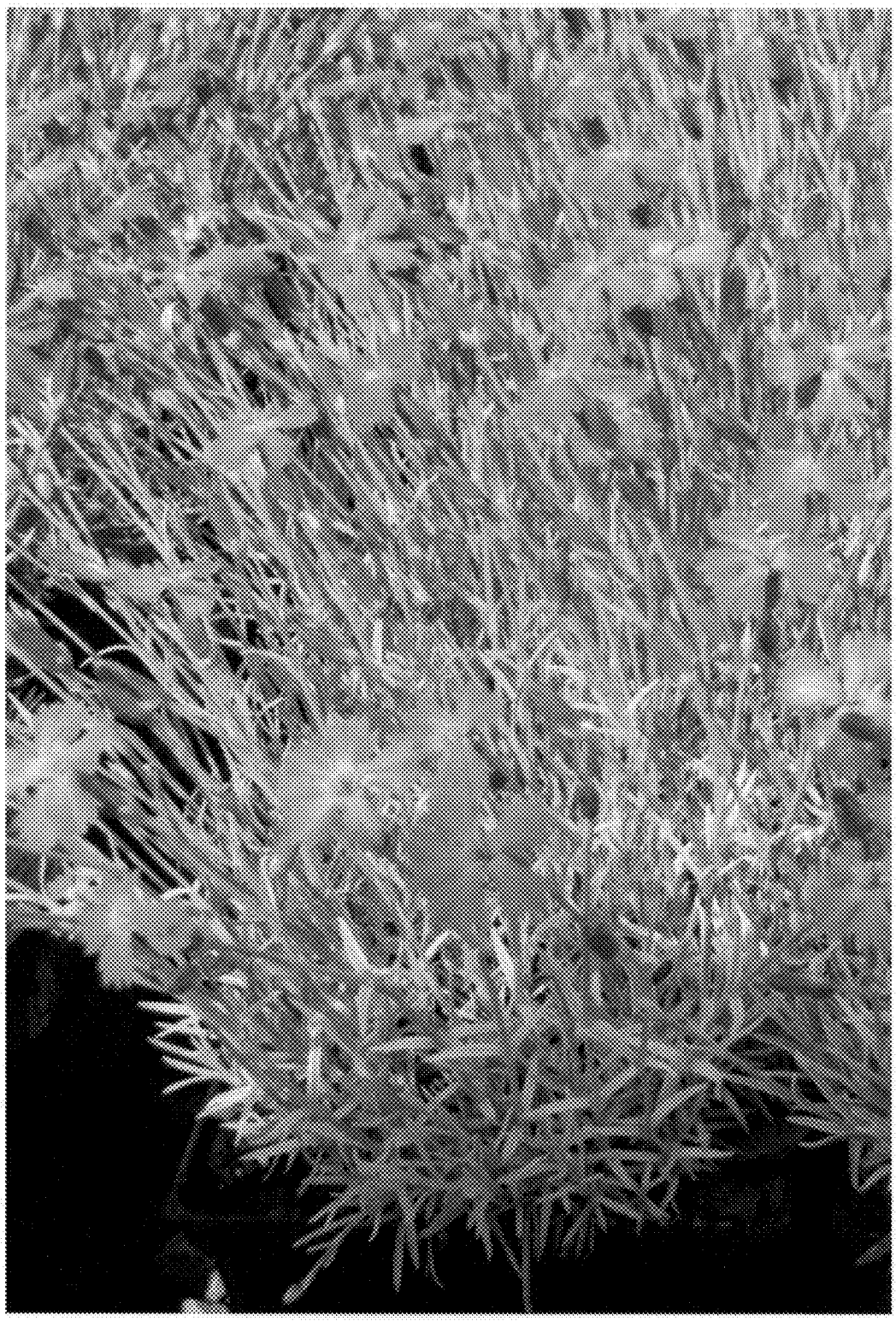
FIG. 1 shows the plant habit of 'Faith' in bloom.
Figure 2:
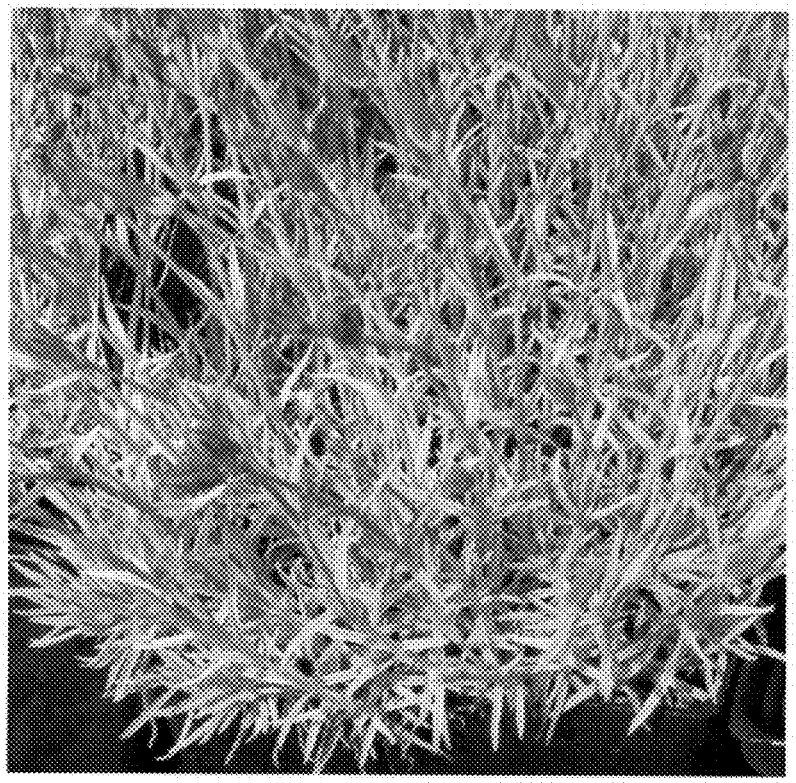
FIG. 2 provides a close-up view of the foliage of 'Faith'.
Figure 3:
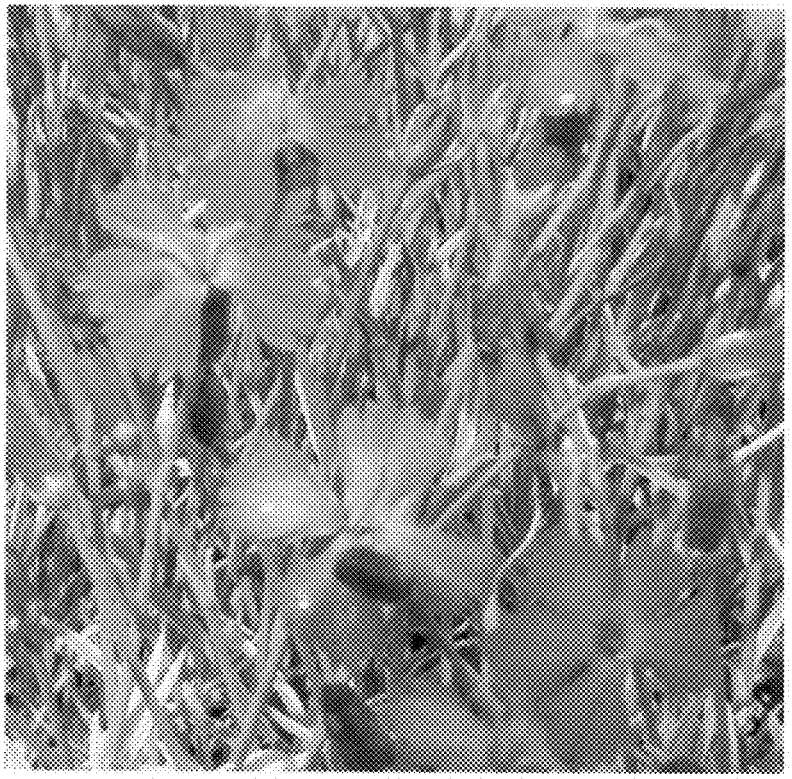
FIG. 3 provides a close-up of the flowers of 'Faith'.

The colors in the photographs may differ slightly from the color values cited in the detailed botanical description, which accurately describe the colors of the new *Dianthus.*

DETAILED BOTANICAL DESCRIPTION

The following is a detailed description of a plant about 12 months in age as grown outside in a 1-quart container in Lewisburg, Tenn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for about 3 weeks in mid spring in Michigan (begins to bloom about one week later than its parent plant, 'Firewitch').

*Plant habit.*—Herbaceous perennial, evergreen, tightly mounded foliage with upright flower scapes.

*Height and spread.*—An average of 15 cm in height and about 15 cm in width.

*Hardiness.*—At least in U.S.D.A. Zones 4 to 9.

*Diseases and pests.*—No susceptibility or resistance to diseases or pests has been observed.

*Root description.*—Fibrous.

Growth and propagation:

*Propagation.*—Stem cuttings and tissue culture (preferred).

*Growth rate.*—Moderate, slow for *Dianthus.*

Stem description:

*Stem strength.*—Strong and held upright.

*Shape.*—Oval, solid swollen at nodes.

*Stem color.*—Young; 138A, mature; 137A; towards base of clump internodes 145B in color, nodes N77A.

*Stem size.*—Average of 1.2 mm in diameter and 8 cm in length (including peduncle).

*Stem surface.*—Glaucous.

*Branching habit.*—Numerous dense branches emerge in whorls from stout woody stems, about 50 lateral branches per plant.

Foliage description:

*Leaf division.*—Simple.

*Leaf shape.*—Linear.

*Leaf base.*—Blunt, clasping to stem.

*Leaf apex.*—Narrowly acute.

*Leaf margin.*—Entire.

*Leaf venation.*—Linear, not conspicuous, color same as leaf color.

*Leaf attachment.*—Sessile, clasping.

*Leaf arrangement.*—Opposite.

*Leaf surface.*—Glaucous.

*Leaf color.*—Newly emerged and mature upper and lower surface; 137A with glaucous coating of 189B, basal clasping portion N144D.

*Leaf size.*—Average of 2.3 cm in length and 3 mm in width with basal portion clasping leaf about 3 mm width and length.

*Foliage fragrance.*—None.

Flower description:

*Inflorescence type.*—Solitary and occasionally pairs of salviform flowers at terminus of lateral branches.

*Lastingness of inflorescence.*—About 4 days.

*Fragrance.*—Sweet.

*Quantity of flowers.*—About 100 flowers per one-gallon plant.

*Flower type.*—Salviform.

*Flower size.*—About 1.7 cm in diameter and 2 cm in depth.

*Flower buds.*—About 1.5 cm in length and 4 mm in width, oblong in shape, color base 138B and apex 70B.

*Peduncle.*—An average of 1 cm in length and 1 mm in diameter, 138A in color, glaucous.

*Pedicel.*—Flowers are sessile to peduncle.

*Petals.*—4, limb is obdeltoid in shape, glabrous surface, rounded apex, margins are serrated along apex and sides and entire at base, limb is about 7 mm in width and length, claw (enclosed in calyx) is an average of 1 cm in length and 3 mm in width, color when opening upper surface; claw 144D, limb 71D, color when opening lower surface; claw 144D, limb 71B, color when mature open upper and lower surface; claw 144D, limb N74C and eye zone 155A, not persistent.

*Calyx.*—Cylindrical in shape, fused sepals with un-fused apex, glaucous, average of 1.2 cm in length and 5 mm in width, 138A to 138C in color, persistent and dries to about 164C in color.

*Sepals.*—5, fused, the triangle-shaped tip at apex are un-fused and about 3 mm in length and 3 mm in width.

*Epicalyx.*—Comprised of 4 involucre bracts; oblong to ovate in shape with truncate base and acute apex, about 6 to 8 mm in length and 3 mm in width, 138B to 138C in color, glaucous.

Reproductive organs:

*Gynoecium.*—Pistil; about 2 cm in length at maturity, extended beyond petals, styles; 155B in color, crystalline in appearance, about 1 cm in length, stigma; 155B in color and curled, ovary; superior, oblong in shape, 7 mm in length and 2.5 mm in width, 144A in color.

*Androecium.*—Stamens; 10, un-fused, about 6 mm in length, filament; 145D in color, about 5 mm in length, very fine and crystalline in appearance, anthers; N80C in color, dorsifixed, oblong in shape, about 1.5 mm in length and 0.5 mm in width, pollen; not discernable.

*Fruit and seed.*—Development of seeds was not observed.

It is claimed:

1. A new and distinct cultivar of *Dianthus* plant named 'Faith' as herein illustrated and described.

* * * * *